United States Patent [19]
Takahashi et al.

[11] Patent Number: 5,994,580
[45] Date of Patent: Nov. 30, 1999

[54] PROCESS FOR PRODUCING ACRYLIC ACID

[75] Inventors: Mamoru Takahashi; Xinlin Tu; Toshiro Hirose; Masakazu Ishii, all of Aichi, Japan

[73] Assignee: Toagosei Co., Ltd., Tokyo, Japan

[21] Appl. No.: 08/955,246

[22] Filed: Oct. 21, 1997

[30] Foreign Application Priority Data

Oct. 21, 1996 [JP] Japan ..................................... 8-297755
Feb. 12, 1997 [JP] Japan ..................................... 9-054200

[51] Int. Cl.⁶ .................................................... C07C 51/16
[52] U.S. Cl. ........................... 562/549; 502/311; 502/312
[58] Field of Search ............................ 562/549; 502/312, 502/311

[56] References Cited

U.S. PATENT DOCUMENTS

| | | | |
|---|---|---|---|
| 3,903,149 | 9/1975 | Kadowaki et al. ...................... | 562/534 |
| 4,260,822 | 4/1981 | Krieger et al. .......................... | 562/549 |
| 5,198,580 | 3/1993 | Bartek et al. ........................... | 562/542 |
| 5,498,588 | 3/1996 | Brazdil et al. .......................... | 502/353 |

FOREIGN PATENT DOCUMENTS

| | | | |
|---|---|---|---|
| 2-180637 | 7/1990 | Japan ............................... | B01J 23/22 |
| 6-279351 | 10/1994 | Japan ............................. | C07C 57/05 |
| 7-10801 | 1/1995 | Japan ............................. | C07C 57/05 |
| 9-157241 | 6/1997 | Japan ........................... | C07C 255/08 |

*Primary Examiner*—Samuel Barts
*Assistant Examiner*—Rosalynd Keys
*Attorney, Agent, or Firm*—Sughrue, Mion, Zinn, Macpeak & Seas, PLLC

[57] ABSTRACT

A process for producing acrylic acid from propane and oxygen gas through a vapor-phase catalytic oxidation reaction, said process comprising conducting the reaction using as a catalyst a metal oxide containing metallic elements Mo, V, Sb, and A (provided that A is at least one element selected from the group consisting of Nb, Ta, Sn, W, Ti, Ni, Fe, Cr, and Co). The metal oxide is prepared by a process including specific steps (1) and (2). The metal oxide may be supported on a compound containing specific elements.

4 Claims, No Drawings

PROCESS FOR PRODUCING ACRYLIC ACID

FIELD OF THE INVENTION

The present invention relates to a process for producing a catalyst for use in processes for producing acrylic acid by vapor-phase catalytic oxidation of propane.

BACKGROUND OF THE INVENTION

Acrylic acid is generally produced by a two-step oxidation process which comprises catalytically reacting propylene with oxygen at high temperature in the presence of a catalyst to produce acrolein and then catalytically reacting the acrolein with oxygen.

In recent years, however, processes for producing acrylic acid from propane through one-step oxidation are being studied in order to reduce the cost of acrylic acid production. The main subject in these studies is to seek for catalysts which give acrylic acid in high yields. Oxidation reaction catalysts for obtaining acrylic acid from propane (hereinafter referred to as "catalysts for acrylic acid production") have been proposed.

Examples thereof include a Bi—Mo—V oxide (see U.S. Pat. No. 5,198,580), an Mo—V—Te oxide (see JP-A-7-10801 and JP-A-6-279351), an Mo—Sb—P oxide (see U.S. Pat. No. 4,260,822), a V—P—Te oxide (see JP-A-3-70445 and *Catal. Today*, Vol. 13, 679 (1992)), and a Bi—Mo—V—Ag oxide (see JP-A-2-83348). (The term "JP-A" as used herein means an "unexamined published Japanese patent application".)

Among the catalysts enumerated above, those with which acrylic acid is obtained in high yields are the Bi-Mo-V oxide and the Mo—V—Te oxide. In the references disclosing the former catalyst, there is a description to the effect that acrylic acid can be produced in a yield of 5% with a selectivity of about 28%. In the references disclosing the latter catalyst, there is a description to the effect that acrylic acid can be obtained in a yield of from 35 to 40% with a selectivity of from 55 to 60%.

In general, the performance of a catalyst does not solely depend on the kinds and proportions of the constituent metals, but considerably depends also on the valences and crystal structures of the constituent metals. It is generally known that the valences and crystal structures of constituent metals contained in catalysts vary depending on catalyst production processes.

The aforementioned Bi—Mo—V oxide catalyst or Mo—V—Te oxide catalyst for acrylic acid production is also produced by a technique intended to impart excellent catalytic performance. Specifically, the technique employed for producing the catalyst comprises evenly mixing telluric acid, ammonium paramolybdate, ammonium metavanadate, or bismuth triacetate, in a heated aqueous medium, evaporating the water to obtain a solid mixture, and calcining the solid mixture at 400 to 600° C. A technique known to be effective in enhancing catalytic performance comprises mixing compounds of antimony, niobium, vanadium, and molybdenum in a heated aqueous medium to obtain a slurry and mixing this slurry with a separately prepared slurry containing a bismuth compound and a molybdenum compound (see U.S. Pat. No. 5,198,580).

On the other hand, catalysts produced from a vanadium compound/antimony compound mixture obtained through the reaction shown by the following scheme (1) are known as catalysts not for the production of acrylic acid, but for producing acrylonitrile by oxidizing propane in the presence of ammonia, i.e., as catalysts for the ammoxidation reaction of propane. Examples of these ammoxidation catalysts include a V—Sb metal oxide (see U.S. Pat. No. 5,498,588 and JP-A-2-180637) and an Mo—V—Sb metal oxide (see JP-A-9-157241).

$$V^{+5} + Sb^{+3} \rightarrow V^{+3} + Sb^{+5} \tag{1}$$

The above reaction is usually conducted using a compound of trivalent antimony, e.g., antimony trioxide, and a compound of pentavalent vanadium, e.g., ammonium metavanadate, in an aqueous medium at a temperature of 80° C. or higher.

However, reaction (1) shown above has not hitherto been employed for producing a catalyst for acrylic acid production.

SUMMARY OF THE INVENTION

The present inventors made intensive investigations on one-step processes for industrially advantageously producing acrylic acid from propane. As a result, they have found that a catalyst containing molybdenum, antimony, vanadium, oxygen, and one or more specific metals as essential components is decreased in the deterioration of catalytic activity and is capable of producing acrylic acid in high yield. The present invention has been completed based on this finding.

The present invention provides, in the first embodiment thereof, a process for producing acrylic acid from propane and an oxygen-containing gas through a vapor-phase catalytic oxidation reaction, the process comprising conducting the reaction using as a catalyst a metal oxide containing metallic elements Mo, V, Sb, and A (provided that A is at least one element selected from the group consisting of Nb, Ta, Sn, W, Ti, Ni, Fe, Cr, and Co).

The present invention further provides, in the second embodiment thereof, a process for producing acrylic acid which comprises conducting the reaction using as a catalyst a metal oxide obtained by depositing at least one compound which contains an element B (provided that B is at least one element selected from the group consisting of Na, K, Rb, Cs, P, and As) as a component thereof on the metal oxide used in the process according to the first embodiment described above and then burning the resulting mixture.

The present invention furthermore provides, in the third embodiment thereof, a process for producing a catalyst which is for use in producing acrylic acid by gas-phase catalytic oxidation of propane and comprises the metal oxide used in the process according to the first embodiment described above, the process comprising the following steps (1) and (2):

step (1): reacting $V^{+5}$ with $Sb^{+3}$ in an aqueous medium at a temperature of 70° C. or more in the presence of $Mo^{+6}$ and, during or after the reaction, bubbling either molecular oxygen or a gas containing molecular oxygen into the reaction mixture; and step (2): adding a compound containing the element A as a component thereof to the reaction product obtained in step (1) above, mixing the ingredients to obtain a homogeneous mixture, and burning the resulting mixture.

DETAILED DESCRIPTION OF THE INVENTION

The present invention is described in detail below.

The metal oxide used in the process according to the first embodiment of the present invention comprises metals comprising essential metallic elements Mo (molybdenum), V (vanadium), Sb (antimony), and A (provided that A is at least one element selected from the group consisting of Nb, Ta, Sn, W, Ti, Ni, Fe, Cr, and Co; the same applies hereinafter) and oxygen. In this metal oxide, the proportions of those metals are preferably represented by the following empirical formula (1):

$$MoV_iSb_jA_k \quad (1)$$

(wherein i, j, and k each is preferably from 0.001 to 3.0, more preferably from 0.01 to 2.0, most preferably from 0.1 to 0.5).

Preferred among the metals represented by A are Nb and Ta.

In the metal oxide described above, if the proportion of V to Mo exceeds 3, combustion reaction is more apt to occur. If the proportion of Sb to Mo exceeds 3, a decreased conversion of propane results. If the proportion of A to Mo exceeds 3, not only a decreased conversion but also a decreased proportion of acrylic acid in the reaction products, i.e., a decreased selectivity, results. If the proportion of any of V, Sb, and A to Mo is below 0.001, the results are a poor conversion of propane and a poor selectivity for acrylic acid.

The proportion of oxygen in the catalyst is fixed by the valences of the elements Mo, Sb, V, and A.

The catalyst described above can be prepared by conventional methods. For example, the catalyst is produced as follows. First, solutions or suspensions respectively containing various compounds containing Mo, Sb, V, and A ("A" has the same meaning as defined above) as components are mixed together in such a proportion that the atomic ratio among the metal components becomes a value within the range specified above. Although the compounds containing those metal components are not particularly limited, preferred examples thereof include oxides, chlorides, hydroxides, ammonium salts, nitrates, and alkoxides.

Specific preferred examples thereof are as follows. Those metal compounds may be used in a proportion corresponding to the metallic composition of the target oxide.

Mo: molybdic acid, ammonium molybdate, molybdenum oxide

V: vanadium oxide, ammonium metavanadate

Sb: antimony chloride, antimony acetate, antimony trioxide

Nb: niobic acid, niobium hydrogen oxalate, niobium oxide, niobium chloride

Ta: tantalic acid, tantalum oxide, tantalum chloride, tantalum ethoxide

Sn: tin oxide, tin hydroxide, stannous chloride, stannic chloride, tin oxalate

W: tungsten oxide, tungstic acid, tungsten chloride, ammonium paratungstate

Ti: ammonium titanium oxalate, titanium butoxide, titanium chloride

Ni: nickel nitrate, nickel oxalate, nickel chloride

Fe: iron nitrate, ferric chloride, iron hydroxide

Cr: chromium nitrate, chromium chloride, chromium oxide

Co: cobalt nitrate, cobalt acetate, cobalt hydroxide, cobalt chloride.

After compounds containing the metal components are mixed by the method described above, or the like, the mixture is dried and calcined in an ordinary way to thereby obtain the target catalyst. Usable drying methods include ordinary drying techniques such as evaporation to dryness, spray drying, and vacuum drying. On the other hand, the calcination is desirably conducted in an inert gas stream, e.g., nitrogen or argon. In such preferred calcination methods, the temperature is preferably from 250 to 1000° C., more preferably from 350 to 900° C. Although the calcination period is not particularly limited, it is preferably from 1 to 20 hours.

The catalyst for use in the process according to the first embodiment of the present invention can be used even in an unsupported state. However, the catalyst may comprise the aforementioned metal components fixed to a support such as, e.g., silica, alumina, silica-alumina, or silicon carbide. For fixing the metal components to these supports, known methods can be employed without particular limitations. For example, a preferred method comprises infiltrating a solution or suspension of compounds containing the aforementioned metal components into a support and then drying and calcining the impregnated support by the methods described above.

The catalyst is not particularly limited in shape, size, particle diameter distribution, or the like, and can have any properties concerning shape and size selected according to the structure of the acrylic acid synthesis reaction vessel to be used. Examples of the catalyst shape include powder and molded forms such as granules, spheres, or solid or hollow cylinders.

After accomplishment of the invention described above, the present inventors made intensive investigations for the purpose of obtaining a catalyst having even higher performance. As a result, the following method was achieved.

Namely, the method achieved is a process for producing a catalyst which is for use in producing acrylic acid by gas-phase catalytic oxidation of propane and comprises a metal oxide containing metallic elements Mo, V, Sb, and A (provided that A is at least one element selected from the group consisting of Nb, Ta, Sn, W, Ti, Ni, Fe, Cr, and Co). This process comprises the following steps (1) and (2):

step (1): reacting $V^{+5}$ with $Sb^{+3}$ in an aqueous medium at a temperature of 70° C. more in the presence of $Mo^{+6}$ and, during or after the reaction, bubbling either molecular oxygen or a gas containing molecular oxygen into the reaction mixture; and step (2): adding a compound containing the element A as a component thereof to the reaction product obtained in step (1) above, mixing the ingredients to obtain a homogeneous mixture, and calcining the resultant mixture.

This process is explained below in more detail.

In step (1) in this process, oxidation-reduction reactions occur among the three reactants, i.e., $Sb^{+3}$, $V^{+5}$, and $Mo^{+6}$, in an aqueous medium at a temperature of 70° C. or higher. The main reaction of these reactions is represented by the following scheme (A).

$$V^{+5}+Sb^{+3} \rightarrow V^{+3}+Sb^{+5} \quad (A)$$

If $Mo^{+6}$ is not present in the reaction system containing the three reactants, the following reaction is known to occur simultaneously with the above reaction [see *Studies in Surface Science and Catalysis*, Vol. 82, p. 281 (1994)].

$$V^{+3}+V^{+5} \rightarrow 2V^{+4} \quad (B)$$

In contrast, in the above process according to the present invention, in which $Mo^{+6}$ coexists, the $V^{+3}$ formed by reaction (A) is rapidly oxidized to $V^{+4}$ by the $Mo^{+6}$. As a result, reaction (B) is inhibited and, hence, most of the $V^{+5}$ used participates in reaction (A).

Preferred examples of the $V^{+5}$ compound which contains $V^{+5}$ as a constituent element and is used in the above-described oxidation-reduction reaction in this process include ammonium metavanadate and vanadium pentoxide. Preferred examples of the $Sb^{+3}$ compound containing $Sb^{+3}$ as a constituent element include antimony trioxide and antimony acetate. Examples of the $Mo^{+6}$ compound containing $Mo^{+6}$ as a constituent element include ammonium molybdate, molybdenum oxide, and molybdic acid. Among these molybdenum compounds, ammonium molybdate is preferred because it is water-soluble.

For the oxidation-reduction reaction, the $Mo^{+6}$, $V^{+5}$, and $Sb^{+3}$ compounds are used in such a proportion that the atomic ratio among the Mo, V, and Sb contained in the target compound to be obtained will be represented by the empirical formula given below. The $V^{+5}$ and $Sb^{+3}$ compounds are used in such a proportion that the $Sb^{+3}/V^{+5}$ atomic ratio is (0.3–1)/1. If the proportion of $Sb^{+3}$ is below 0.3, a decreased selectivity for acrylic acid results. If the proportion thereof exceeds 1, a decreased conversion of propane results.

The oxide contains Mo, V, Sb, and A in a proportion represented by the following empirical formula (1):

$$MoV_iSb_jA_k \qquad (1)$$

(wherein i, j, and k each is from 0.001 to 3.0).

Preferably, A is Nb or Ta, and i and j each is from 0.01 to 1.5, provided that j/i is from 0.3 to 1. Especially preferably, i and j each is from 0.1 to 1.

If i or j in the above empirical formula is below 0.01 or above 1.5, the reaction for producing acrylic acid results in a poor conversion of propane and a poor selectivity for acrylic acid.

The total feed amount of those three metal compounds is from 3 to 30 parts by weight per 100 parts by weight of the aqueous medium. If the total amount of the three metal compounds exceeds 30 parts by weight, part of the vanadium compound or molybdenum compound remains undissolved and the oxidation-reduction reaction is apt to proceed incompletely.

The reaction described above does not proceed at temperatures lower than 70° C. Preferred reaction temperatures are around the boiling point of the aqueous medium. The reaction time is preferably about from 5 to 15 hours.

The degree of progress of the reaction can be determined by determining the amount of pentavalent antimony present in the reaction mixture and comparing this found value with the amount of the trivalent antimony fed initially. Specifically, the amount of pentavalent antimony contained in the reaction mixture obtained can be determined by adding 1 N aqueous oxalic acid solution to the reaction mixture in an amount at least 10 times the amount of the reaction mixture to thereby precipitate the antimony only, and then titrating the precipitate with hydriodic acid.

The valences of the molybdenum and vanadium contained in the reaction mixture can be determined, e.g., by electron spin resonance spectrometry.

In this process, molecular oxygen (hereinafter referred to as "oxygen gas") or a gas containing oxygen gas (inclusively referred to as "oxygen-containing gas") is bubbled into the oxidation-reduction reaction mixture as stated above. The bubbling of an oxygen-containing gas into the oxidation-reduction reaction mixture may be conducted either during or after the oxidation-reduction reaction. During the bubbling of an oxygen-containing gas, the reaction mixture is preferably kept being stirred.

By bubbling an oxygen-containing gas into the oxidation-reaction mixture, a catalyst having high performance can be obtained as in Examples 10 and 11 described hereinafter.

The oxygen gas concentration in the oxygen-containing gas is preferably 0.5 vol % or higher, more preferably from 1 to 20 vol %, and most preferably from 2 to 15 vol % (hereinafter abbreviated as %). If the oxygen-containing gas has an oxygen gas concentration lower than 0.5%, the catalyst finally obtained may have a decreased activity.

The preferred range of the rate of bubbling (flow rate) depends on the amount of the oxidation-reduction reaction mixture. When the amount of the reaction mixture is about from 200 to 500 ml, the rate of bubbling is preferably from 3 to 12 l/hr.

The period of the bubbling of an oxygen-containing gas into the reaction mixture is preferably 4 hours or longer, and more preferably from 5 to 10 hours. If the period of bubbling of an oxygen-containing gas is shorter than 4 hours, the catalyst obtained may have a decreased activity.

As to how the molecular oxygen introduced by the bubbling of an oxygen-containing gas into the reaction mixture reacts with compounds present in the reaction mixture has not been elucidated. However, from the determination of $Mo^{+5}$ in the reaction mixture, it has been ascertained that the $Mo^{+6}$ which oxidizes $V^{+3}$ to $V^{+4}$ in the present invention is first reduced to $Mo^{+5}$, part of which thereafter returns to $Mo^{+6}$ again. It is presumed from the above chemical changes that the molecular oxygen serves to oxidize the $Mo^{+5}$.

In this process, the metal A (provided that A is at least one element selected from the group consisting of Nb, Ta, Sn, W, Ti, Ni, Fe, Cr and Co) is added to either the dispersion which is the reaction mixture resulting from the above reaction and contains molybdenum, vanadium, and antimony, or a solid matter obtained by subjecting the dispersion to evaporation to dryness. These ingredients are mixed together to give a homogeneous mixture. The metal A preferably Nb or Ta. Examples of the niobium or tantalum compound include niobium oxide, niobic acid, tantalum oxide, and tantalic acid. Although the niobium or tantalum compound may be used as an aqueous dispersion thereof, the compound is preferably used in the form of an aqueous solution of, e.g., the corresponding oxalate prepared by using oxalic acid.

The niobium or tantalum compound is used in such an amount as to give a catalyst in which the atomic ratio of niobium or tantalum to molybdenum is (0.001–3.0)/1. If the proportion of niobium or tantalum to molybdenum in the catalyst obtained is below 0.001/1, this catalyst deteriorates. If that proportion exceeds 3.0, the catalyst has low activity and a reduced conversion of propane results.

The mixture of metal compounds obtained through the procedure described above is burned, if necessary after being dried by evaporation to dryness, spray drying, etc. The mixture is thus converted to the metal oxide to be used as a catalyst in the present invention.

The calcination can be conducted under conditions generally employed for the production of metal oxide catalysts. Specifically, the calcination conditions preferably include a temperature of from 300 to 900° C. and a calcination period of from 1 to 20 hours, and more preferably include a temperature of from 450 to 700° C. and a period of from 1 to 2 hours. Where an oxalate was added as the fourth metal compound after the preparation of a mixture comprising compounds of molybdenum, vanadium, and antimony, the calcination is especially preferably conducted first at around 300° C. for about 5 hours and then at around 600° C. for about 2 hours. The atmosphere for calcination is preferably an inert gas stream, such as nitrogen or argon, or air. More preferred is the inert gas stream because a catalyst having higher activity is obtainable therewith.

The metal oxide obtained by the process described above was analyzed by X-ray powder diffractometry (X-ray source: Cu—$K_\alpha$ line). The results obtained were compared with those for a metal oxide obtained by conducting the same procedure as the above except that the bubbling of an oxygen-containing gas during the heating of the compounds of molybdenum, vanadium, and antimony in an aqueous medium was omitted. The comparison revealed that the relative intensity of the peak at a diffraction angle $2\theta$ of 28.1 for the metal oxide according to the invention was about ½ to ⅓ of that for the other metal oxide, showing that the two oxides differed in crystal structure.

The contents of metal elements in the metal oxide obtained through the burning can be ascertained by fluorescent X-ray spectrometry.

In using the thus-obtained composite metal oxide as a catalyst for acrylic acid production, the oxide is preferably pulverized to an appropriate particle size to increase the surface area thereof. For the pulverization, either a dry or a wet method can be used. Examples of usable pulverizers include mortars and ball mills. The particle size of the catalyst is preferably 20 jm or smaller, and more preferably 5 $\mu$m or smaller.

In the process according to the second embodiment of the present invention, a compound containing an element B (B is at least one element selected from the group consisting of Na, K, Rb, Cs, P, and As; the same applies hereinafter; this compound is referred to as "compound B") as a component thereof is deposited on the oxide obtained above (hereinafter referred to as "supporting oxide"). The deposition amount of the compound B is preferably from 0.001 to 0.3, and more preferably from 0.002 to 0.1, in terms of the atomic ratio of the element B to the molybdenum contained in the supporting oxide. If the atomic ratio of the element B to molybdenum is below 0.001, a decreased selectivity for acrylic acid results. If that atomic ratio exceeds 0.3, a decreased conversion of propane results because the active surface of the supporting oxide is covered with an oxide of the element B.

Examples of the compound B include sodium compounds such as sodium carbonate, sodium hydrogen carbonate, sodium hydroxide, sodium nitrate, and sodium oxide; potassium compounds such as potassium hydroxide, potassium hydrogen carbonate, potassium carbonate, potassium nitrate, potassium acetate, and potassium oxide; rubidium compounds such as rubidium hydroxide, rubidium carbonate, rubidium nitrate, and rubidium oxide; cesium compounds such as cesium oxide, cesium carbonate, cesium acetate, cesium hydroxides, and cesium nitrate; phosphorus compounds such as phosphoric acid, phosphorus oxide, and diammonium hydrogen phosphate; and arsenic compounds such as arsenic chloride, arsenic trioxide, and arsenic pentoxide. Preferred among the elements represented by B are K, Rb, and P.

A preferred method for depositing a compound B on the supporting oxide comprises mixing a solution prepared by dissolving the compound B in water or an organic solvent such as alcohol with a powder of the supporting oxide. The concentration of the compound of B in the solution is preferably from 0.1 to 1.0 mol/l. The amount of the solution is preferably from 20 to 50 parts by weight per 100 parts by weight of the supporting oxide.

After the solution of the compound B is mixed with the powder of the supporting oxide, the mixture is stirred to homogenize the same as much as possible. The solvent in the resulting mixture is vaporized, e.g., by evaporation to dryness, whereby a metal oxide powder having the compound B deposited thereon can be obtained. Calcining the thus-obtained metal oxide powder at 300 to 500° C. for 1 to 5 hours gives the target metal oxide for use as a catalyst.

The thus-obtained oxide having a compound B fixed thereto can be used even in an unsupported state. The oxide can also be used after being fixed to a support having an appropriate particle size, such as silica, alumina, silica-alumina, or silicon carbide.

In the processes for producing acrylic acid according to the present invention, the starting materials, i.e., propane and an oxygen-containing gas, are introduced simultaneously into a reactor and reacted with each other in the presence of the catalyst. It is also possible to introduce propane and an oxygen-containing gas into a reactor either separately or as a mixture thereof prepared beforehand.

A commercial propane as such can be utilized as the starting propane without subjecting the commercial product to a special treatment. However, the purity of the propane is desirably as high as possible, from the standpoint of inhibiting side reactions, etc. Examples of the oxygen-containing gas as the other starting material include air, oxygen gas, and gaseous mixtures obtained by diluting these with an inert gas such as, e.g., nitrogen, steam, or carbon dioxide. However, air is optimal from the standpoints of safety and cost.

The mixing ratio between the propane and the oxygen-containing gas is not particularly limited. However, where the oxygen-containing gas for use in the reaction is air, the amount thereof is preferably up to 30 times by volume the amount of the propane, and more preferably in the range of from 0.2 to 20 times.

Reaction systems of different catalyst packing types can be utilized without particular limitations. Examples thereof include fixed-bed, moving-bed, and fluidized-bed systems.

Reaction conditions are not particularly limited. However, the reaction temperature is preferably from 300 to 600° C., and more preferably from 350 to 500° C. The reacting mixture gas is preferably fed at a space velocity (hereinafter referred to as "SV") of from 300 to 5,000 $hr^{-1}$.

In the production of acrylic acid from propane, the reaction yields by-products such as, e.g., propylene, carbon monoxide, carbon dioxide, and acetic acid besides acrylic acid as the target compound. These by-products can be separated from the acrylic acid by a purification operation based on differences in boiling point, e.g., distillation. Among the by-products, the isolated propylene, which serves as an intermediate for acrylic acid, can be utilized again in the reaction after being mixed with feedstock propane. In this case, however, the propylene is desirably mixed in an amount up to 20 vol % based on the propane so as to avoid adverse influences on the reaction.

The present invention will be explained below in more detail by reference to Examples and Comparative Examples, but the invention should not be construed as being limited to these Examples.

EXAMPLE 1

Into a 500-ml glass flask was introduced 259 ml of distilled water. Thereto was added 12.3 g of ammonium metavanadate. This mixture was heated with stirring to dissolve the salt. Thereafter, 12.7 g of antimony trioxide was added, and this mixture was heated with ref luxing for 12 hours. To the resulting mixture were successively added 61.0 g of ammonium molybdate and a solution prepared by dissolving 26.3 g of oxalic acid and 6.5 g of niobic acid in 180 ml of distilled water with heating at 50° C. This mixture was stirred at 50° C. for 30 minutes. The slurry thus obtained was concentrated by heating, dried at 120° C. for 3 hours, and then calcined in a nitrogen stream at 600° C. for 2 hours to obtain a catalyst in which the Mo/Sb/V/Nb atomic ratio was 1.0/0.25/0.3/0.1. The catalyst obtained was pulverized to 16- to 30-mesh particles. Thereafter, a 1.5 g portion (volume: 1.5 ml) of the particles was packed into an 8-mm$\phi$ reaction tube made of quartz. A mixed gas composed of 4.4 vol % propane, 7.0 vol % oxygen, 26.3 vol % nitrogen, and 62.3 vol % steam was fed to the reaction tube at an SV of 1,800 hr$^{-1}$ to react the mixed gas at a temperature of 400° C. for 10 hours. The results obtained are shown in Table 1 below. The conversion of propane (%) and the selectivity for acrylic acid (%) shown in Table 1 were calculated using the following equations (from the number of moles of each compound).

Conversion of propane (%)
=[(propane fed)−(unreacted propane)]/(propane fed)
Selectivity for acrylic acid (%)
=(acrylic acid yielded)/[(propane fed)−(unreacted propane)]

In the catalyst composition shown in Table 1, symbol X, which indicates the proportion of oxygen, is fixed by the valences of the other elements.

EXAMPLE 2

Using the same catalyst as in Example 1, reaction was conducted under the same conditions as in Example 1, except that the reaction temperature was changed to 410° C. The results obtained are shown in Table 1 below.

EXAMPLE 3

Using the same catalyst as in Example 1, a mixed gas composed of 4.4 vol % propane, 7.0 vol % oxygen, 57.6 vol % nitrogen, and 31.0 vol % steam was reacted for 10 hours under the conditions of an SV of 1,800 hr$^{-1}$ and a temperature of 380° C. The results obtained are shown in Table 1 below.

EXAMPLE 4

Into a 500-ml glass flask was introduced 259 ml of distilled water. Thereto was added 12.3 g of ammonium metavanadate. This mixture was heated with stirring to dissolve the salt. To this solution were successively added 26.0 g of antimony acetate, 61.0 g of ammonium molybdate, and a solution prepared by dissolving 26.3 g of oxalic acid and 6.5 g of niobic acid in 180 ml of distilled water with heating. This mixture was stirred at 50° C. for 30 minutes. The subsequent procedure was conducted in the same manner as in Example 1 to prepare a catalyst in which the Mo/Sb/V/Nb atomic ratio was 1.0/0.25/0.3/0.1. The catalyst obtained was pulverized to 16- to 30-mesh particles. Thereafter, a 1.5 g portion (volume: 1.5 ml) of the particles was used to react a mixed gas composed of 4.4 vol % propane, 7.0 vol % oxygen, 26.3 vol % nitrogen, and 62.3 vol % steam for 10 hours under the conditions of an SV of 1,800 hr$^{-1}$ and a temperature of 380° C. The results obtained are shown in Table 1 below.

COMPARATIVE EXAMPLE 1

Into a 500-ml glass flask was introduced 259 ml of distilled water. Thereto was added 12.3 g of ammonium metavanadate. This mixture was heated with stirring to dissolve the salt. To the resulting solution were successively added 61.0 g of ammonium molybdate and a solution prepared by dissolving 26.3 g of oxalic acid and 6.5 g of niobic acid in 180 ml of distilled water with heating. This mixture was stirred at 50° C. for 30 minutes. The slurry thus obtained was concentrated by heating, dried at 120° C. for 3 hours, and then burned in a nitrogen stream at 600° C. for 2 hours to obtain a catalyst in which the Mo/V/Nb atomic ratio was 1.0/0.3/0.1. The catalyst obtained was pulverized to 16- to 30-mesh particles. Thereafter, a 1.5 g portion (volume: 1.5 ml) of the particles was packed into an 8-mm$\phi$ reaction tube made of quartz, and reaction was conducted under the same conditions as in Example 1. The results obtained are shown in Table 1 below.

COMPARATIVE EXAMPLE 2

A catalyst was prepared in the same manner as in Comparative Example 1, except that 21.1 g of copper nitrate was additionally added. In this catalyst, the Mo/Cu/V/Nb atomic ratio was 1.0/0.25/0.3/0.1. Using the thus-obtained catalyst, reaction was conducted in the same manner as in Example 1. The results obtained are shown in Table 1 below.

COMPARATIVE EXAMPLE 3

A catalyst was prepared in the same manner as in Comparative Example 1, except that 42.2 g of bismuth nitrate was additionally added. In this catalyst, the Mo/Bi/V/Nb atomic ratio was 1.0/0.25/0.3/0.1. Using the thus-obtained catalyst, reaction was conducted in the same manner as in Example 1. The results obtained are shown in Table 1 below.

TABLE 1

| | Catalyst composition | Feedstock composition (vol %) propane/oxygen/nitrogen/steam | SV (hr$^{-1}$) | Reaction temperature (° C.) | Conversion of propane (%) | Selectivity for acrylic acid (%) |
|---|---|---|---|---|---|---|
| Example 1 | MoSb$_{0.25}$V$_{0.3}$Nb$_{0.1}$O$_x$ | 4.4/7.0/26.3/62.3 | 1800 | 400 | 30.9 | 29.5 |
| Example 2 | MoSb$_{0.25}$V$_{0.3}$Nb$_{0.1}$O$_x$ | 4.4/7.0/26.3/62.3 | 1800 | 410 | 34.1 | 23.3 |
| Example 3 | MoSb$_{0.25}$V$_{0.3}$Nb$_{0.1}$O$_x$ | 4.4/7.0/57.5/31.2 | 1800 | 380 | 19.3 | 21.1 |
| Example 4 | MoSb$_{0.25}$V$_{0.3}$Nb$_{0.1}$O$_x$ | 4.4/7.0/26.3/62.3 | 1800 | 380 | 21.5 | 6.8 |
| Comparative Example 1 | MoV$_{0.3}$Nb$_{0.1}$O$_x$ | 4.4/7.0/26.3/62.3 | 1800 | 400 | 21.1 | 0.8 |
| Comparative Example 2 | MoCu$_{0.25}$V$_{0.3}$Nb$_{0.1}$O$_x$ | 4.4/7.0/26.3/62.3 | 1800 | 400 | 30.0 | 0.3 |
| Comparative Example 3 | MoBi$_{0.25}$V$_{0.3}$Nb$_{0.1}$O$_x$ | 4.4/7.0/26.3/62.3 | 1800 | 400 | 21.0 | 2. |

EXAMPLE 5

To 130 ml of distilled water placed in a 300-ml glass flask was added 6.15 g of ammonium metavanadate. This mixture was heated with stirring to dissolve the salt. Thereto were added 6.35 g of antimony trioxide and 30.5 g of ammonium molybdate. An air/nitrogen mixed gas having an oxygen gas concentration of 15% was bubbled into the resultant liquid mixture at a flow rate of 100 ml/min while stirring the mixture with a stirrer at 360 rpm at an elevated temperature of 92° C. Thus, the mixture was reacted for 5 hours.

The resulting blue colloidal dispersion was cooled to room temperature. An aqueous solution which had been prepared by dissolving 13.15 g of oxalic acid and 3.25 g of niobic acid in 90 ml of distilled water and had ordinary temperature was added to the dispersion. This mixture was vigorously agitated for 30 minutes, concentrated by heating, and then subjected to evaporation to dryness at 120° C.

The solid thus obtained was calcined in a nitrogen gas stream at 600° C. for 2 hours to obtain a metal oxide catalyst. Atomic ratio in this metal oxide was Mo/Sb/V/Nb=1.0/0.25/0.3/0.12.

To 5.0 g of the metal oxide obtained above (hereinafter referred to as "oxide a") was added a solution prepared by dissolving 0.030 g of potassium hydrogen carbonate in 1 g of distilled water. After this mixture was sufficiently mixed, it was dried at 120° C. for 1 hour and then calcined at 350° C. for 2 hours to obtain a catalyst. The catalyst was pulverized to 16- to 30-mesh particles and packed into a reactor.

The catalyst obtained was examined by fluorescent X-ray spectrometry. As a result, the Mo/Sb/V/Nb/K atomic ratio therein was found to be 1.0/0.25/0.3/0.12/0.013.

A mixed gas composed of 4.4 vol % propane, 7.0 vol % oxygen, 26.3 vol % nitrogen, and 62.3 vol % steam (hereinafter referred to as "test gas") was fed to the reactor at an SV of 1,600 hr$^{-1}$ while maintaining the temperature of the reactor at 400° C. The conversion of propane, selectivity for acetic acid, selectivity for propylene, and selectivity for acrylic acid in the above reaction were calculated respectively using the following equations. The results obtained are shown in Table 2 below.

EXAMPLE 6

Reaction was conducted under the same conditions as in Example 5, except that the reaction temperature was changed to 420° C. The results of the reaction are shown in Table 2 below.

EXAMPLES 7 AND 8

Catalysts were produced in the same manner as in Example 5, except that in place of potassium hydrogen carbonate, each of the metal compounds shown in Table 2, i.e., diammonium hydrogen phosphate (use amount: 0.03 g) and rubidium nitrate (use amount: 0.044 g), was fixed to the oxide "a". Reaction was conducted in the same manner as in Example 5, except that each of the catalysts thus obtained was used. The results obtained are shown in Table 2 below.

EXAMPLE 9

To 5.0 g of the oxide "a" obtained in Example 5 was added a solution prepared by dissolving 0.030 g of potassium hydrogen carbonate in 1 g of distilled water. After this mixture was sufficiently mixed, it was dried at 120° C. for 1 hour. Thereto was added a solution prepared by dissolving 0.040 g of diammonium hydrogen phosphate as the second ingredient in 1 g of distilled water. After this mixture was sufficiently mixed, it was calcined at 350° C. for 2 hours.

The catalyst thus obtained was pulverized to 16- to 30-mesh particles and packed into a reactor. The test gas described above was reacted under the conditions of a temperature of 400° C. and an SV of 1,600 hr$^{-1}$. The results obtained are shown in Table 2 below.

TABLE 2

| Compound added | Conversion of propane (%) | Selectivity for acetic acid (%) | Selectivity for propylene (%) | Selectivity for acrylic acid (%) |
| --- | --- | --- | --- | --- |
| Example 5 potassium hydrogen carbonate | 35.0 | 5.9 | 3.1 | 72.6 |
| Example 6 potassium hydrogen carbonate | 48.8 | 6.5 | 2.5 | 68.5 |
| Example 7 diammonium hydrogen phoaphate | 31.7 | 8.9 | 4.5 | 63.7 |
| Example 8 ruhidium nitrat9 | 29.6 | 5.4 | 5.4 | 68.6 |
| Example 9 potassium hydrogen carbonate, diammonium hydrogen phosphate | 32.1 | 4.7 | 4.3 | 69.5 |

In the Examples shown in Table 2, the reaction was conducted at 400° C., except that the reaction temperature in Example 6 was 420° C.

EXAMPLES 10 AND 11

The oxide "a" obtained in Example 5 was used as a catalyst to react the test gas under the conditions of an SV of 3,200 (Example 10) or 4,800 (Example 11) and a temperature of 400° C. The results obtained are shown in Table 3 below.

TABLE 3

| | Space velocity (hr$^{-1}$) | Conversion of propane (%) | Selectivity for acetic acid (%) | Selectivity for propylene (%) | Selectivity for acrylic acid (%) |
| --- | --- | --- | --- | --- | --- |
| Example 10 | 3200 | 31.9 | 9.1 | 5.5 | 60.8 |
| Example 11 | 4800 | 22.5 | 7.2 | 13.6 | 61.1 |

While the invention has been described in detail and with reference to specific embodiments thereof, it will be apparent to one skilled in the art that various changes and modifications can be made therein without departing from the spirit and scope thereof.

What is claimed is:

1. A process for producing acrylic acid from propane and oxygen gas through a vapor-phase catalytic oxidation reaction, said process comprising conducting the reaction using as a catalyst a metal oxide containing metallic elements Mo, V, Sb, and A (provided that A is at least one element selected from the group consisting of Nb, Ta, Sn, W, Ti, Ni, Fe, Cr, and Co), said catalyst consisting essentially of Mo, V, Sb and A.

2. The process for producing acrylic acid as claimed in claim 1, wherein the metal oxide contains Mo, V, Sb, and A in a proportion represented by the following empirical formula (1):

$$MoV_iSb_jA_k \quad (1)$$

wherein i, j, and k each is from 0.001 to 3.0.

3. The process for producing acrylic acid as claimed in claim 1, wherein the amount of the oxygen contained in the catalyst is fixed by the valences of the elements Mo, V, Sb, and A.

4. A process for producing acrylic acid from propane and oxygen gas through a vapor-phase catalytic oxidation reaction, said process comprising conducting the reaction using as a catalyst a metal oxide obtained by depositing at least one compound which contains an element B (provided that B is at least one element selected from the group consisting of Na, K, Rb, Cs, P, and As) as a component thereof on a metal oxide which contains metallic elements Mo, V, Sb, and A (provided that A is at least one element selected from the group consisting of Nb, Ta, Sn, W, Ti, Ni, Fe, Cr, and Co) and calcining the resultant mixture, wherein said catalyst consists essentially of Mo, V, Sb, A and B.

* * * * *